(12) United States Patent
Jethmalani et al.

(10) Patent No.: US 6,851,804 B2
(45) Date of Patent: Feb. 8, 2005

(54) READJUSTABLE OPTICAL ELEMENTS

(76) Inventors: Jagdish M. Jethmalani, 11018 W. Ocean Air Dr., Apt. 368, San Diego, CA (US) 92130; Shiao H. Chang, 1420 San Carlos Rd., Arcadia, CA (US) 91006

( * ) Notice: Subject to any disclaimer, the term of this patent is extended or adjusted under 35 U.S.C. 154(b) by 0 days.

(21) Appl. No.: 10/324,540

(22) Filed: Dec. 19, 2002

(65) Prior Publication Data

US 2003/0174375 A1 Sep. 18, 2003

Related U.S. Application Data

(60) Provisional application No. 60/344,182, filed on Dec. 28, 2001.

(51) Int. Cl.[7] .............................. C08K 5/34; A61F 2/14; A61F 2/16; G02C 7/00
(52) U.S. Cl. ................... 351/159; 351/160 R; 351/176; 359/581; 359/642; 359/831; 359/838; 359/858; 359/890; 385/14; 385/141; 623/6.6; 623/6.62; 623/6.16
(58) Field of Search ................................ 359/581, 642, 359/831, 838, 858, 890; 385/14, 141; 351/159, 160 R, 176; 623/6.6, 6.62, 5.16; 522/34, 75, 99, 148, 172; 523/106, 107, 108

(56) References Cited

U.S. PATENT DOCUMENTS

| | | | |
|---|---|---|---|
| 3,741,628 A | | 6/1973 | Margerum |
| 4,148,987 A | * | 4/1979 | Winey .......................... 526/316 |
| 4,719,248 A | * | 1/1988 | Bambury et al. ............ 523/108 |
| 5,098,445 A | * | 3/1992 | Hung et al. ..................... 8/507 |
| 5,534,558 A | * | 7/1996 | Minns .......................... 522/35 |
| 5,621,017 A | | 4/1997 | Kobayakawa et al. |
| 5,891,931 A | * | 4/1999 | Leboeuf et al. ............... 522/64 |
| 5,989,462 A | * | 11/1999 | Buazza et al. ............. 264/1.36 |
| 6,132,462 A | * | 10/2000 | Li .............................. 623/6.11 |
| 6,218,463 B1 | | 4/2001 | Molock et al. |
| 6,465,588 B1 | * | 10/2002 | Li .............................. 526/258 |
| 2003/0125409 A1 | * | 7/2003 | Lai .............................. 522/34 |

FOREIGN PATENT DOCUMENTS

WO   WO99/18139   *   4/1999

* cited by examiner

*Primary Examiner*—Susan Berman

(57) ABSTRACT

The invention relates to optical elements whose optical properties can be repeatedly adjusted over time. Through the use of modifying compositions capable of stimulus induced polymerization coupled with a blend of stimulus absorbers and initiators, it is possible to repeatedly adjust the optical properties of the element by exposing the lens to a stimulus which exceeds the absorption capacity of the stimulus absorber.

8 Claims, 3 Drawing Sheets

READJUSTABLE OPTICAL ELEMENTS

The present application claims the benefit of the priority data in U.S. application Ser. No. 60/344,182, filed Dec. 28, 2001.

BRIEF SUMMARY OF THE INVENTION

The invention relates to optical elements whose optical properties can be readjusted over extended periods of time. In one embodiment, an intraocular lens is provided whose optical properties can be changed multiple times after implantation.

BACKGROUND OF THE INVENTION

Approximately two million cataract surgery procedures are performed in the United States annually. The procedure generally involves making an incision in the anterior lens capsule to remove the cataractous crystalline lens and implanting an intraocular lens in its place. The power of the implanted lens is selected (based upon pre-operative measurements of ocular length and corneal curvature) to enable the patient to see without additional corrective measures (e.g., glasses or contact lenses). Unfortunately, due to errors in measurement, and/or variable lens positioning and wound healing, about half of all patients undergoing this procedure will not enjoy optimal vision without correction after surgery. Brandser et al, *Acta Ophthalmol Scand* 75:162–165 (1997); Oshika et al., *J. Cataract Refract Surg* 24:509–514 (1998). Because the power of prior art intraocular lenses generally cannot be adjusted once they have been implanted, the patient typically must choose between replacing the implanted lens with another lens of a different power or be resigned to the use of additional corrective lenses such as glasses or contact lenses. Since the benefits typically do not outweigh the risks of the former, it is almost never done.

Recently, a new type of intraocular lens has been described which permits post-operative manipulation of the optical properties of the lens. This allows for post-operative adjustment of the lens to achieve optimal vision quality for the patient. The post-operative manipulation is accomplished through the polymerization of modifying composition ("MC") in specific regions of the lens by external stimuli, such as light. By polymerizing the MC in specific regions, the optical qualities of the lens can be adjusted until the desired optical properties are achieved. To prevent further changes in the optical properties, however, any remaining MC is then polymerized throughout the lens, "locking-in" the properties.

Unfortunately, this prevents further adjustment of the lens at a later time. For example, if the lens were implanted in a child, it would not be possible to readjust the lens to compensate for changes in vision due to aging or the like. In this case, the patient would have to choose between surgery to replace the lens or to use other corrective devices, e.g., glasses.

Thus, a need exists for an intraocular lens whose optical properties can be adjusted on more than one occasion.

SUMMARY OF THE INVENTION

The invention relates to optical elements whose optical properties can be modified post-fabrication and adjusted multiple times. In a specific embodiment, an intraocular lens is provided whose optical properties can be adjusted post-implantation more than once.

The optical properties of the elements are adjusted by the localized stimulus-induced polymerization of a modifying composition ("MC") which is dispersed in the optical element. When the MC is polymerized in a specific region of the element, the optical properties of the element are changed, This is accomplished by changing the refractive index of the element in the area where polymerization has occurred, or by changing the shape of the element, or both. One key aspect of the invention is that this is accomplished with the addition or removal of material from the element.

As noted above, the polymerization of the MC is stimulus-induced. Typically, this refers to photopolymerization; however, other external stimuli may be used. The stimulus-induced polymerization is caused by the presence of one or more initiators which, when exposed to the proper stimulus, induces or initiates polymerization of the MC.

The invention relates to controlling the conditions under which the initiators start polymerization of the MC. It has been found that through the use of various stimulus-absorbing compounds combined with initiator compounds, it is possible to control the conditions under which the polymerization reaction occurs. Thus, it is possible to control the conditions such that any external stimuli present in the normal environment encountered by the element will not cause polymerization of the MC.

DETAILED DESCRIPTION OF THE INVENTION

Figure 1:
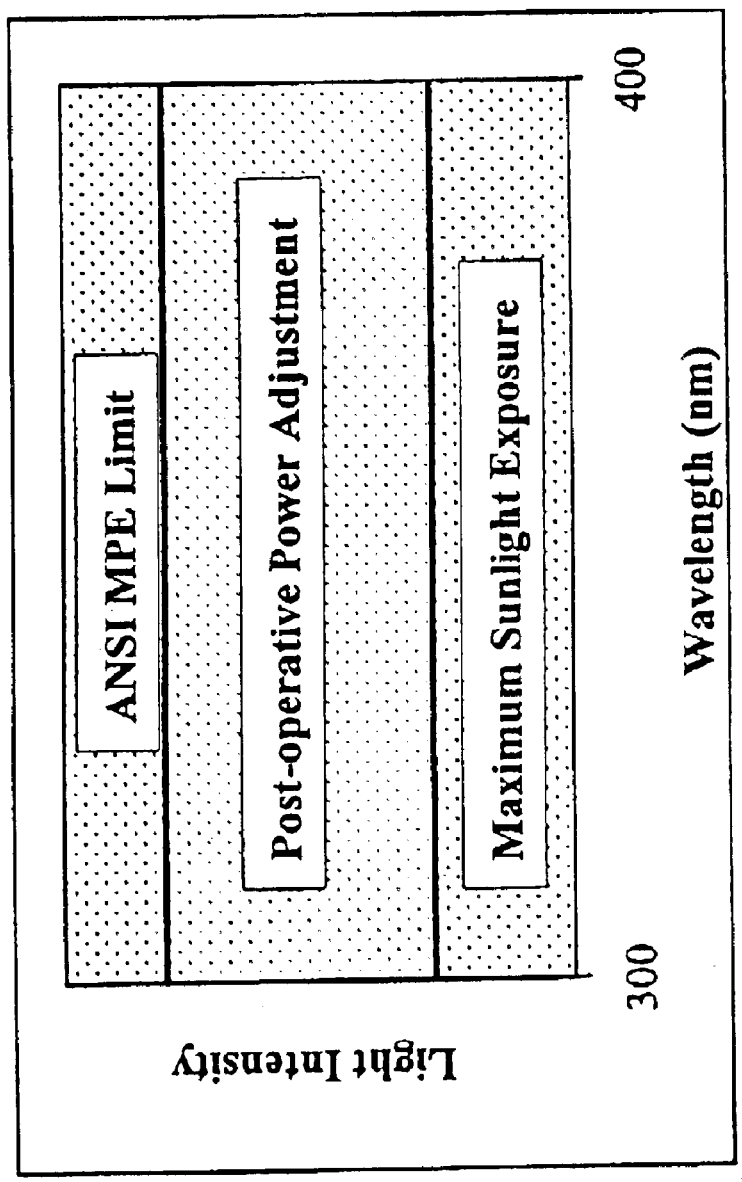
FIG. 1 is a plot of light intensity versus wave length showing the levels for ambient sunlight and the ANSI MPE level.
Figure 2:
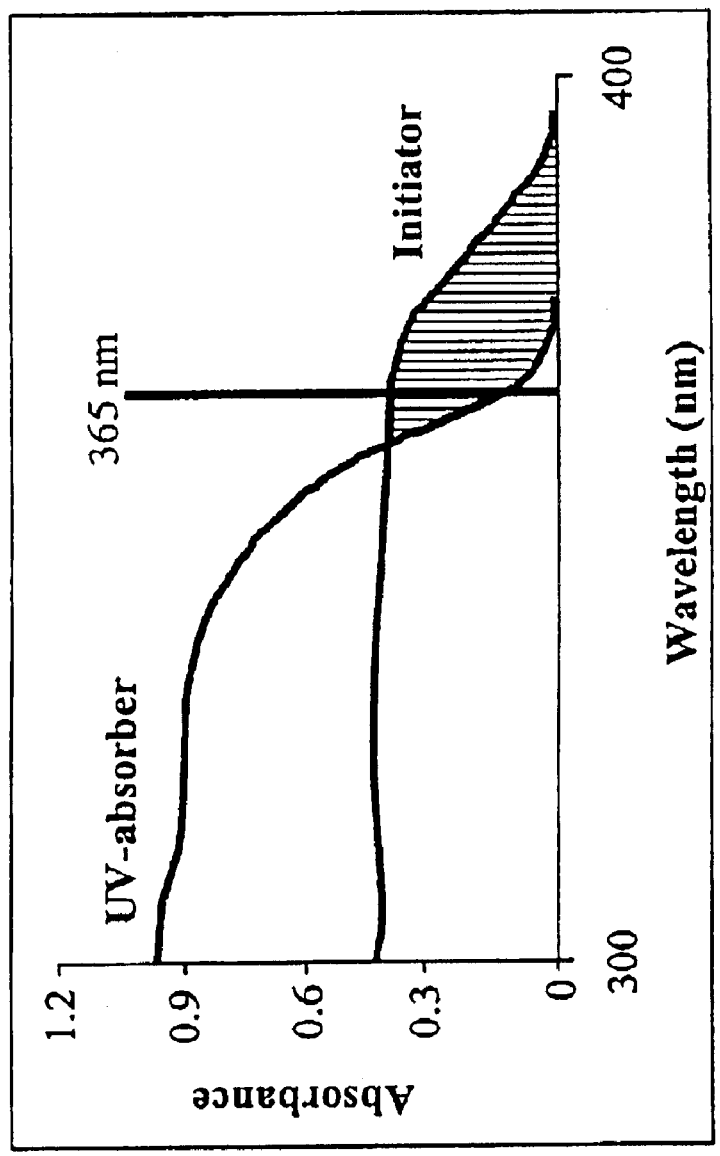
FIG. 2 is a plot of UV absorber versus wave length for a UV absorber and initiator combination useful in practice of the invention.

The invention relates to optical elements whose optical properties can be continuously modified or adjusted over its useful life. This adjustment is accomplished in a self-contained system that is without the addition or removal of material from the element.

Typical optical elements within the scope of the invention include data storage elements, including compact disks, digital video disks; lenses, including but not limited to spectacle lenses; contact lenses, intraocular lenses; mirrors, prisms, and the like. In the preferred embodiment, the optical element is an intraocular lens.

The optical element is typically prepared from a first polymer matrix which gives shape to the element as well as many of its physical properties such as hardness, flexibility and the like.

The optical element also contains a MC dispersed therein. This MC may be a single compound or a combination of compounds that is capable of stimulus-induced polymerization, preferably photopolymerization.

The nature of the first polymer matrix and the MC will vary depending upon the end use contemplated for the optical element. However, as a general rule, the first polymer matrix and the MC are selected such that the components that comprise the MC are capable of diffusion within the first polymer matrix. Put another way, a loose first polymer matrix will tend to be paired with larger MC components and a tight first polymer matrix will tend to be paired with smaller MC components.

Upon exposure to an appropriate energy (e.g., heat or light), the MC typically forms a second polymer matrix in the exposed region of the optical element. The presence of the second polymer matrix changes the material characteristics of this portion of the optical element to modulate its refraction capabilities. In general, the formation of the second polymer matrix typically increases the refractive index of the affected portion of the optical element. After exposure, the MC in the unexposed region will migrate into the exposed region over time. The amount of MC migration into the exposed region is time dependent and may be precisely controlled. If enough time is permitted, the MC components will re-equilibrate and redistribute throughout optical element (i.e., the first polymer matrix, including the exposed region). When the region is re-exposed to the energy source, the MC that has since migrated into the region (which may be less than if the MC were allowed to re-equilibrate) polymerizes to further increase the formation of the second polymer matrix. This process (exposure followed by an appropriate time interval to allow for diffusion) may be repeated until the exposed region of the optical element has reached the desired property (e.g., power, refractive index, or shape). At this point, because of the presence of the UV absorber, no further polymerization occurs until the element is exposed to the specific wave length and intensity. Thus, in the case of an intraocular lens, the lens may be exposed to natural light and the like without further changes in the lens. If adjustment are needed because of aging or changes in the patient's health, for example, the lens can be adjusted by exposure to an appropriate energy source.

The first polymer matrix is a covalently or physically linked structure that functions as an optical element and is formed from a first polymer matrix composition ("FPMC"). In general, the first polymer matrix composition comprises one or more monomers that upon polymerization will form the first polymer matrix. The first polymer matrix composition optionally may include any number of formulation auxiliaries that modulate the polymerization reaction or improve any property of the optical element. Illustrative examples of suitable FPMC monomers include acrylics, methacrylates, phosphazenes, siloxanes, vinyls, homopolymers and copolymers thereof. As used herein, a "monomer" refers to any unit (which may itself either be a homopolymer or copolymer) which may be linked together to form a polymer containing repeating units of the same. If the FPMC monomer is a copolymer, it may be comprised of the same type of monomers (e.g., two different siloxanes) or it may be comprised of different types of monomers (e.g., a siloxane and an acrylic).

In one embodiment, the one or more monomers that form the first polymer matrix are polymerized and cross-linked in the presence of the MC. In another embodiment, polymeric starting material that forms the first polymer matrix is cross-linked in the presence of the MC. Under either scenario, the MC components must be compatible with and not appreciably interfere with the formation of the first polymer matrix. Similarly, the formation of the second polymer matrix should also be compatible with the existing first polymer matrix. Put another way, the first polymer matrix and the second polymer matrix should not phase separate and light transmission by the optical element should be unaffected.

As described previously, the MC may be a single component or multiple components so long as: (i) it is compatible with the formation of the first polymer matrix; (ii) it remains capable of stimulus-induced polymerization after the formation of the first polymer matrix: and (iii) it is freely diffusable within the first polymer matrix. In preferred embodiments, the stimulus-induced polymerization is photo-induced polymerization.

In general, there are two types of intraocular lenses ("IOLs"). The first type of an intraocular lens replaces the eye's natural lens. The most common reason for such a procedure is cataracts. The second type of intraocular lens supplements the existing lens and functions as a permanent corrective lens. This type of lens (sometimes referred to as a phakic intraocular lens) is implanted in the anterior or posterior chamber to correct any refractive errors of the eye. In theory, the power for either type of intraocular lenses required for emmetropia (i.e., perfect focus on the retina from light at infinity) can be precisely calculated. However, in practice, due to errors in measurement of corneal curvature, and/or variable lens positioning and wound healing, it is estimated that only about half of all patients undergoing IOL implantation will enjoy the best possible vision without the need for additional correction after surgery. Because prior art IOLs are generally incapable of post-surgical power modification, the remaining patients must resort to other types of vision correction such as external lenses (e.g. glasses or contact lenses) or cornea surgery. The need for these types of additional corrective measures is obviated with the use of the intraocular lenses of the present invention.

The inventive intraocular lens comprises a first polymer matrix and a MC dispersed therein. The first polymer matrix and the MC are as described above with the additional requirement that the resulting lens be biocompatible.

Illustrative examples of a suitable first polymer matrix include: polyacrylates such as polyalkyl acrylates and polyhydroxyalkyl acrylates; polymethacrylates such as polymethyl methacrylate ("PMMA"), a polyhydroxyethyl methacrylate ("PHEMA"), and polyhydroxypropyl methacrylate ("HPMA"); polyvinyls such as polystyrene and polyvinylpyrrolidone ("NVP"); polysiloxanes such as polydimethylsiloxane; polyphosphazenes, and copolymers of thereof. U.S. Pat. No. 4,260,725 and patents and references cited therein (which are all incorporated herein by reference) provide more specific examples of suitable polymers that may be used to form the first polymer matrix.

In preferred embodiments, the first polymer matrix generally possesses a relatively low glass transition temperature ("$T_g$") such that the resulting IOL tends to exhibit fluid-like and/or elastomeric behavior. In applications where flexibility is important (e.g., intraocular lenses or contact lenses), the $T_g$ will generally be less than 25° C. preferably less than 20° C. Where rigidity is important, the $T_g$ will be much higher, e.g., 25° C. to 50° C.

The first polymer matrix is typically formed by cross-linking one or more polymeric starting materials wherein each polymeric starting material includes at least one cross-linkable group. Illustrative examples of suitable cross-linkable groups include but are not limited to hydride, acetoxy, alkoxy, amino, anhydride, aryloxy, carboxy, enoxy, epoxy, halide, isocyano, olefinic, and oxine. In more preferred embodiments, each polymeric starting material includes terminal monomers (also referred to as endcaps) that are either the same or different from the one or more monomers that comprise the polymeric starting material but include at least one cross-linkable group. In other words, the terminal monomers begin and end the polymeric starting material and include at least one cross-linkable group as part of its structure. Although it is not necessary for the practice of the present invention, the mechanism for cross-linking the polymeric starting material preferably is different than the mechanism for the stimulus-induced polymerization of the components that comprise the MC. For example, if the MC is polymerized by photo-induced polymerization, then it is preferred that the polymeric starting materials have cross-linkable groups that are polymerized by any mechanism other than photo-induced polymerization.

An especially preferred class of polymeric starting materials for the formation of the first polymer matrix is polysiloxanes (also known as "silicones") endcapped with a terminal monomer which includes a cross-linkable group selected from the group consisting of acetoxy, amino, alkoxy, halide, hydroxy, and mercapto. Because silicone IOLS tend to be flexible and foldable, generally smaller incisions may be used during the IOL implantation procedure. An example of an especially preferred polymeric starting material is bis(diacetoxymethylsilyl)-polydimethysiloxane (which is polydimethylsiloxane that is endcapped with a diacetoxymethylsilyl terminal monomer).

The MC that is used in fabricating IOLs is as described above except that it has the additional requirement of biocompatibility. The MC is capable of stimulus-induced polymerization and may be a single component or multiple components so long as: (i) it is compatible with the formation of the first polymer matrix; (ii) it remains capable of stimulus-induced polymerization after the formation of the first polymer matrix; and (iii) it is freely diffusable within the first polymer matrix. In general, the same type of monomers that is used to form the first polymer matrix may be used as a component of the MC. However, because of the requirement that the MC monomers must be diffusable within the first polymer matrix, the MC monomers generally tend to be smaller (i.e., have lower molecular weights) than the monomers which form the first polymer matrix. In addition to the one or more monomers, the MC may include other components such as initiators and sensitizers that facilitate the formation of the second polymer matrix.

Because of the preference for flexible and foldable IOLs, an especially preferred class of MC monomers is polysiloxanes endcapped with a terminal siloxane moiety that includes a photopolymerizable group. An illustrative representation of such a monomer is:

wherein Y is a siloxane which may be a monomer, a homopolymer or a copolymer formed from any number of siloxane units, and X and $X^1$ may be the same or different and are each independently a terminal siloxane moiety that includes a photopolymerizable group. Illustrative examples of Y include:

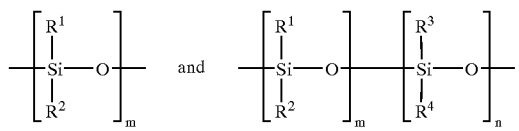

wherein: m and n are independently each an integer and $R^1$, $R^2$, $R^3$, and $R^4$, are independently each hydrogen, alkyl (primary, secondary, tertiary, cyclo), aryl, or heteroaryl. In preferred embodiments, $R^1$, $R^2$, $R^3$, and $R^4$, is a $C_1$–$C_{10}$ alkyl or phenyl. Because MC monomers with a relatively high aryl content have been found to produce larger changes in the refractive index of the inventive lens, it is generally preferred that at least one of $R^1$, $R^2$, $R^3$, and $R^4$ is an aryl, particularly phenyl. In more preferred embodiments. $R^1$, $R^2$, $R^3$ are the same and are methyl, ethyl or propyl and $R^4$ is phenyl.

Illustrative examples of X and $X^1$ (or $X^1$ and X depending on how the MC polymer is depicted) are:

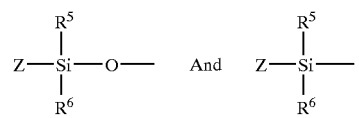

respectively wherein:
$R^5$ and $R^6$ are independently each hydrogen, alkyl, aryl, or heteroaryl; and
Z is a photopolymerizable group.

In preferred embodiments $R^1$ and $R^6$ are independently each a $C_1$ and $C_{10}$ alkyl or phenyl and Z is a photopolymerizable group that includes a moiety selected from the group consisting of acrylate, allyloxy, cinnamoyl, methacrylate, stibenyl, and vinyl. In more preferred embodiments, $R^5$ and $R^6$ is methyl, ethyl, or propyl and Z is a photopolymerizable group that includes an acrylate or methacrylate moiety.

In especially preferred embodiments, an MC monomer is of the following formula:

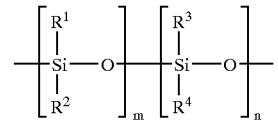

wherein X and $X^1$ are the same and $R^1$, $R^2$, $R^3$, and $R^4$ are as defined previously. Illustrative examples of such MC monomers include dimethylsiloxane-diphenylsiloxane copolymer endcapped with a vinyl dimethylsilane group; dimethylsiloxane-methylphenylsiloxane copolymer endcapped with a methacryloxypropyl dimethylsilane group; and dimethylsiloxane endcapped with a methacryloxypropyldimethylsilane group. Although any suitable method may be used, a ring-opening reaction of one of more cyclic siloxanes in the presence of triflic acid has been found to be a particularly efficient method of making one class of inventive MC monomers. Briefly, the method comprises contacting a cyclic siloxane with a compound of the formula:

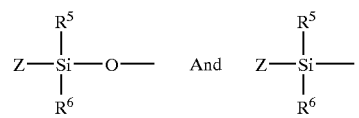

in the presence of triflic acid wherein $R^5$, $R^6$, and Z are as defined previously. The cyclic siloxane may be a cyclic siloxane monomer, homopolymer, or copolymer. Alternatively, more than one cyclic siloxane may be used. For example, a cyclic dimethylsiloxane tetramer and a cyclic methyl-phenylsiloxane trimer are contacted with bis-methacryloxypropyltetramethyldisiloxane in the presence of triflic acid to form a dimethyl-siloxane methyl-phenylsiloxane copolymer that is endcapped with a methacryloxylpropyl-dimethylsilane group, an especially preferred MC monomer.

As discussed above, the stimulus-induced polymerization requires the presence of an initiator. The initiator is such that upon exposure to a specific stimuli, it induces or initiates the polymerization of the MC. In the preferred embodiment, the initiator is a photoinitiator. The photoinitiator may also be associated with a sensitizer. Examples of photoinitiators suitable for use in the practice of the invention are acetophenones (e.g., substituted haloaceto phenones and diethoxyacetophenone); 2,4-dichloromethyl-1,3,5-triazines; benzoin methyl ether; and O-benzoyl oximino ketone.

Suitable sensitizers include p-(dialkylamino aldehyde); n-alkylindolylidene; and bis [p-(dialkyl amino) benzylidene] ketone.

Alternatively, the MC of the invention may comprise multifunctional acrylate based monomers having the general formula:

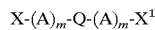

or

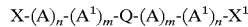

wherein Q is an acrylate based compound used to create the acrylate monomer; A and $A^1$ are the same or different and have the general structure:

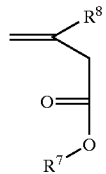

wherein $R^7$ and $R^8$ are alkly, haloalkyl, aryl, haloaryl, and X and $X^1$ contain moieties capable of stimulus induced polymigration, preferably photopolymerizable groups and N and M are integers.

In one embodiment the macromer has the general structure

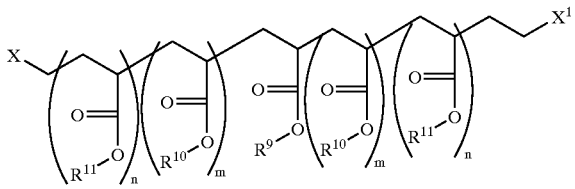

wherein $R^9$ $R^{10}$ and $R^{11a}$ are independently selected from the group consisting of alkyls, haloalkyls, aryls, and haloaryls and n and m are integers and X and $X^1$ are as defined above.

Another key component of the invention is a stimulus absorbing compound. These compounds regulate the level of external stimulus needed to initiate the polymerization of the MC.

In the preferred embodiment, the stimulus-absorbing compound is a light-absorbing compound, more preferably a UV absorber. UV absorbers useful in the practice of this invention include benzotriazole compounds having the general formula:

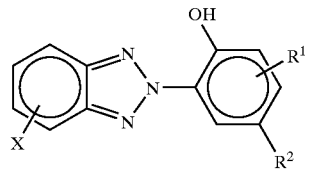

and mixtures thereof, wherein X is selected from the group consisting of H, alkoxy radicals preferably containing 1 to about 6 carbon atoms, and halogen, $R_1$ is selected from the group consisting of H and alkyl radicals, preferably containing 1 to about 8 carbon atoms, provided that at least one of X and $R_1$ is other than H, and $R_2$ is an organic radical, preferably an alkenyl radical, with a terminal double bond. The alkoxy radical is preferably selected from the group consisting of methyl radical and t-alkyl radicals containing 4 to about 6 carbon atoms. The present compositions, including the covalently bonded ultraviolet light absorbing component preferably are capable of absorbing ultraviolet light in the range of about 300 nm to about 400 nm.

As with the photoabsorber, the preferred photoinitiator useful in the practice of the invention are UV-sensitive photoinitiators. Particularly preferred photoinitiators are x-alkyl/benzoins having the general formula or structure:

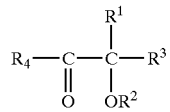

wherein $R^1$ is H, alkyl radical, aryl radical, substituted alkyl, or substituted aryl radical, and $R^2$ is H, alkyl radical, aryl radical, substituted alkyl or substituted aryl radical; $R^3$ and $R^4$ are phenyl or substituted phenyl. Specific examples of $R^4$ and $R^2$ groups include methyl, phenyl trifluoropropyl, ethyl and cyano propyl. Phenyl substituents from the $R^3$ and $R^4$ groups may include alkyl, alkoxy, halogen, alkyaryl, cyano alkyl, haloalkyl and N, N dialkyl amino. Photoinitiator useful in the practice of the invention include Irgacure 819, Irgacure 184, Irgacure 369 and Irgacure 651 all available from Ciba Specialty Chemicals Inc. Where clarity is required, such as in optical elements, Irgacure 651 is preferred.

Also useful in the practice of the invention are photoinititators having two initiators linker by a short polymer backbone. One such compound is Benzoin polydimethyl siloxane Benzoin (B-pdms-B) wherein two benzoin moieties are linked by a dimethyl siloxane bridge. The compound has the general formula:

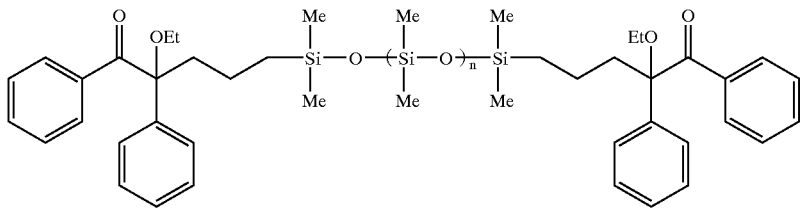

n = 2 or 2–28

Synthesis of these compounds is described in U.S. Pat. No. 4,477,326, the teachings of which are incorporated by reference for United States practice.

The relative amounts of UV absorber and initiator will vary depending upon the desire degree of absorbence for the specific application. Generally the ratio of photoinitiator to UV absorber will range from about 6:1 to about 25:1. Generally, the relative amounts of photoinitiator and UV absorber can be calculated using the formula:

$$\cos T = A = \in_1 b_1 c_1 + \in_2 b_2 c_2$$

wherein T is transmittance, A is absorbence, $\in_1$ is the extinction coefficient for the UV absorber, $b_1$ is the path length of the light and $c_1$ is the concentration of the UV absorber. $\in_2$, $b_2$, and $c_2$ are as defined above except that they relate to the photoinitiator. In practice, it has been found that the actual absorbence is generally less than the predicted values such that the amount use should generally be al least 1.5 times the calculated amount.

The photoinitiator and UV absorber are combined with the polymers, monomers or macromers to be polymerized or cross-linked. In one embodiment, the photoinitiator is bound to the macromers. In other embodiments, the photoinitiator remains free in the mixture.

While the above illustration is stated in terms of ultraviolet-based initiators and absorbers, the same principles apply to other initiator/absorber combinations. For example, the initiator may be activated by infra-red radiation. In that case, an infra-red absorbing compound must be used to control the activation. The same is true for other stimulus sources, such as light.

A key advantage of the optical element of the present invention is that an element property may be modified post-fabrication. In the case of an IOL, for example, the modification may be made after implantation within the eye. For example, any errors in the power calculation due to imperfect corneal measurements and/or variable lens positioning and wound healing may be modified in a post surgical outpatient procedure. Additionally, corrections due to physical changes in the patient over time can also be made.

In addition to the change in the element's refractive index, the stimulus-induced formation of the second polymer matrix has been found to affect the element's power by altering the shape of the element in a predictable manner. For example, in one embodiment, formation of the second polymer matrix changes the thermodynamic equilibrium in this element. This in turn promotes the migration of the MC which in turn can cause a change in the curvature of the lens. As a result, both mechanisms may be exploited to modulate an IOL property, such as power, after it has been implanted within the eye. In general, the method for implementing an inventive optical element having a first polymer matrix and a MC dispersed therein comprises:

(a) exposing at least a portion of the optical element to a stimulus whereby the stimulus induces the polymerization of the MC. This step may be shipped if the element possesses the desired initial properties;

(b) determining that a change in optical properties is required or desired;

(c) exposing or reexposing at least a portion of the element to a stimulus whereby the stimulus induces polymerization of the MC to cause a change in optical properties of the element;

(d) waiting for a period of time;

(e) evaluating the performance of the element.

After exposure to an external stimulus, the element may need to be reexposed to stimulus until the desired optical properties are achieved.

In another embodiment, wherein an optical element's properties need to be modified, a method for modifying the element comprises:

(a) exposing a first portion of the optical element to a stimulus whereby the stimulus induces the polymerization of the MC; and (b) exposing a second portion of the lens to the stimulus.

The first element portion and the second element portion represent different regions of the lens although they may overlap. Optionally, the method may include an interval of time between the exposures of the first element portion and the second element portion. In addition, the method may further comprise re-exposing the first element portion and/or the second element portion any number of times (with or without an interval of time between exposures) or may further comprise exposing additional portions of the element (e.g., a third element portion, a fourth element portion, etc.)

In general, the location of the one or more exposed portions will vary depending on the type of refractive error being corrected. For example, in one embodiment, the exposed portion of the IOL is the optical zone which is the center region of the lens (e.g., between about 4 mm and about 5 mm in diameter). Alternatively, the one or more exposed lens portions may be along IOL's outer rim or along a particular meridian. In another embodiment, different regions of a spectacle lens can be exposed to a stimulus thereby creating a bifocal spectacle lens. In preferred embodiments, the stimulus is light. In more preferred embodiments, the light is from a laser source.

Once the desired correction is made, there is no need for further exposure to the stimulus to "lock in" the shape or properties. The presence of the absorber compound will prevent further changes in the element until the element is exposed to a stimulus of the correct frequency and intensity. This allows the optical element to be used once the initial adjustment is made and, if needed, the optical properties can be readjusted, in situ. In the case of an intraocular lens, this means that after the initial adjustment, the patent can return for future adjustment due to factors such as age or the like, over the life of the lens. In another embodiment, spectacles can be created whose corrective qualities can be repeatedly adjusted, eliminating the need for new lenses as the patient's vision changes.

Figure 5:
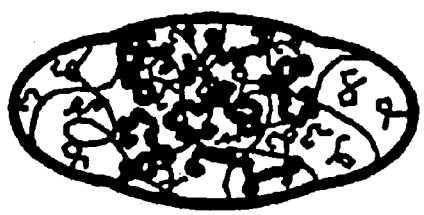
FIG. 5 is a cross section of a portion of an optical element of the invention after exposure to UV light.
Figure 4:
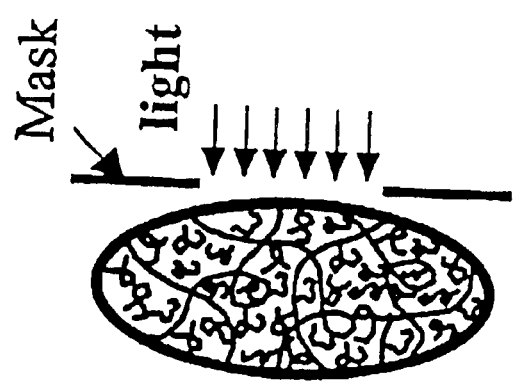
FIG. 4 is a cross section of an optical element of the present invention upon exposure to UV light.
Figure 3:
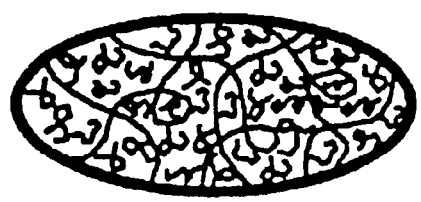
FIG. 3 is a cross section of a portion of an optical element of the invention.

Through the focused use of external stimulus, such as UV light, it is possible to cause polymigration of the MC in specific regions of the optical element. This includes controlling the depth of the second matrix as well as where the matrix is located in relation to the center of the element. FIGS. 3 through 5 illustrate this concept.

FIG. 3 shows a portion of a cross section of an optical element of the invention showing the first polymer matrix, 11 and the modifying composition 12 dispersed within the first polymer matrix.

FIG. 4 reflects the exposure of the optical element to UV light in a predetermined pattern, duration and intensity. The UV absorber in the exposed region prevents polymerization of the MC until the absorption level of the UV absorber is exceeded. Then the inhibitor is triggered resulting in polymerization of the MC to form a second polymer matrix. Formation of the matrix, however, only occurs when the absorbence capacity of the UV absorber has been exceeded. There it is possible to limit the depth of the second polymer matrix by limiting the intensity and duration of the exposure to UV light. FIG. 5 represents such a limited matrix formation. The second polymer matrix only expands part way through the optical element with optical properties different than the unmodified regions. Further exposures of the optical element to UV light can then be used to alter the optical properties further.

As noted above, those adjustments can be made during the course of the initial adjustment or can occur weeks or years later. Thus, as the needs of the users change over time, the optical properties can be adjusted without the need for surgery or the like.

The readjustable properties of the optical element can also lead to novel data storage devices. By controlling the region where the second polymer matrix is found, it is possible to record data in three dimensions and then add or change the data stored at a later time.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

EXAMPLES

The following examples are offered by way of example and are not intended to limit the scope of the invention in any manner.

A series of siloxane slabs were prepared as reflected in the tables below. In the control experiments, Part A consisted of a silicone polymer Silicone MED 6820. Part B was prepared by mixing Silicone 6820 with a catalyst Pt-divinyltetramethyldisiloxane complex. Parts A and B were separately degassed to remove any air and then blended together. The mixture was then degassed and placed into a 1 mm thick mold where it was held in a Carver press for 48 hours at approx. 1000 psi and at 40° C.

The experimental sections were prepared in the same manner except that a blend of modifying composition, UV absorber and UV initiator was first prepared and then added to Part A. The proportions of the components were as listed in Table I. The modifying composition (identified as CalAdd in Table I) was methacrylate endcapped dimethylsiloxane diphenylsiloxane copolymer with a Mn of from 700 to 1000.

In the table below, the initiators used consisted generally of the following compounds, Irgacure 651, a commercially available UV initiator made by Ciba Specialty Chemicals, Inc.; Initiator B-pdms-B which is a blend of dual benzoin structures having the general structure

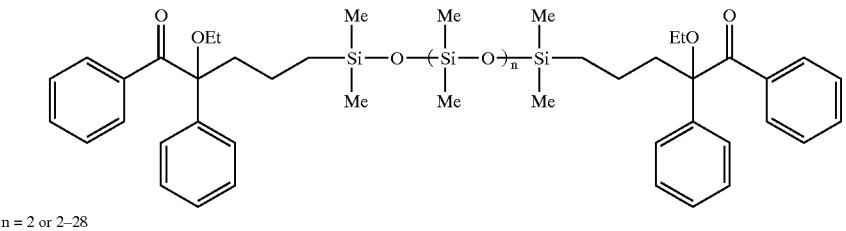

n = 2 or 2–28 wherein n ranges from 2 to 28, and B-L4-B which has the same general structure as above except with n=2 only. Use of these initiators are preferred for applications where clarity is essential such as optical elements. In other applications where clarity is not essential, the use of other initiators such as Irgacure 369 is acceptable. Again, the key is to use an initiator that is triggered in the desire range of wavelengths and does not require an intensity in excess of prescribed safety standards.

In the experiments recited in the table below, the ultraviolet absorbing compound used is UVAM a commercially available absorber. While the use of UVAM is preferred, other ultraviolet absorbing compounds may be used.

In the experiments reported in Table I, polymer slabs were prepared as described above. Sections of the slab were then taken and exposed to light at 365 nm for 30 to 120 minutes at intensities ranging from 0.0 to 8 milliwatts per square centimeters. The transmission and absorbence of the UV light through the section was determined by Differential Photocalorimetric Analyzer and reported in the table as 10% Transmittance and ΔH (heat of polymerization).

TABLE I

| Experiment | Part A Wt % | Part B Wt % | Irg 651 Wt % | B-L4-B Wt % | B-pdms-B Wt % | UVAM Wt % | Cal. Add Wt % | Intensity mW/cm² | Environ. | ΔH J/g | 10% T |
|---|---|---|---|---|---|---|---|---|---|---|---|
| Control | 34.9 | 34.9 | 0.23 | | | | 29.97 | 4.82 | N₂ | −20.584 | 290 nm |
| | | | | | | | | 3.11 | Air | −18.586 | |
| 2 | 34.9 | 34.9 | 0.23 | | | 0.04 | 29.93 | 4.82 | N2 | −25.832 | 384 nm |
| | | | | | | | | 3.11 | Air | −11.575 | |
| 3 | 46.7 | 33.3 | 0.23 | | | 0.02 | 19.75 | 9.61 | N2 | −6.397 | 363 nm |
| | | | | | | | | 9.7 | Air | −8.742 | |
| 4 | 46.70 | 33.3 | 0.23 | | | 0.02 | 19.75 | 9.61 | N2 | −2.839 | 361 nm |
| | | | | | | | | 9.61 | Air | −8.156 | |
| 5 | 36.3 | 33.3 | 0.46 | | | 0.02 | 29.92 | 6.7 | N2 | 15.631 | 364 |
| | | | | | | | | 6.59 | Air | −21.363 | |
| | | | | | | | | 8.66 | Aqueous | −25.473 | |
| | | | | | | | | 6.77 | | −27.273 | |
| | | | | | | | | 6.37 | | −19.545 | |
| | | | | | | | | 4.33 | | −23.183 | |
| | | | | | | | | 087 | | −17.785 | |
| 6 | 36.3 | 33.2 | | | 0.5 | 0.02 | 29.98 | 6.68 | N2 | −18.36 | 323 |
| | | | | | | | | 6.68 | Air | −13.025 | |
| 7 | 36.2 | 33.1 | | | 0.75 | 0.03 | 29.82 | 7.49 | N2 | −20.231 | 364 nm |
| | | | | | | | | 3.74 | | −17.483 | |
| | | | | | | | | 7.49 | Air | −16.890 | |
| | | | | | | | | 3.74 | | −2.654 | |
| | | | | | | | | 7.96 | Aqueous | −19.147 | |
| | | | | | | | | 5.92 | | −21.672 | |
| | | | | | | | | 3.98 | | −20.231 | |
| | | | | | | | | 0.796 | | −21.880 | |
| 8 | 35.2 | 33.1 | | .75 | | .04 | 29.78 | 7.86 | Air | −10.275 | 383 nm |
| 9 | 36.1 | 33.1 | | 1.0 | | 0.04 | 29.76 | 7.86 | Air | −13.931 | 383 nm |
| | | | | | | | | 8.05 | Aqueous | −22,899 | |
| | | | | | | | | 6.26 | | −18.322 | |
| | | | | | | | | 5.92 | | −29.994 | |
| | | | | | | | | 4.03 | | −18710 | |
| | | | | | | | | 0.85 | | −11.459 | |
| 10 | 36 | 32.9 | | 1.0 | | 0.04 | 30.096 | 6.89 | Air | −10.015 | 387 nm |
| | | | | | | | | 3.56 | | −7.835 | |
| | | | | | | | | 3.45 | | −6.062 | |
| | | | | | | | | 2.07 | | −3.062 | |
| | | | | | | | | 7.36 | Aqueous | −20.009 | |
| | | | | | | | | 4.81 | | −18.071 | |
| | | | | | | | | 2.4 | | −15.171 | |
| | | | | | | | | 0.74 | | −11.869 | |
| | | | | | | | | 0.01 | | −9.219 | |
| 11 | 36 | 32.9 | | | 1.0 | 0.04 | 30.096 | 6.98 | Air | −11.366 | 383 |
| | | | | | | | | 4.01 | | −9.002 | |
| | | | | | | | | 2.13 | | −6.163 | |
| | | | | | | | | .0.71 | | −1.45 | |
| | | | | | | | | 7.36 | Aqueous | −14.484 | |
| | | | | | | | | 4.6 | | −15.295 | |
| | | | | | | | | 2.59 | | −16.449 | |
| | | | | | | | | 0.74 | | −13.819 | |
| | | | | | | | | 0.097 | | −13.819 | |

What is claimed is:

1. An optical element comprising:
   a first polymer matrix;
   a modifying composition for modifying the properties of said optical element dispersed throughout the first polymer matrix; the modifying composition being capable of stimulus-induced polymerization;
   a blend of a light absorbing compound and an initiator.

2. The optical element of claim 1 wherein said stimulus is light.

3. The optical element of claim 2 wherein said initiator is a photoinitiator.

4. The optical element of claim 3 wherein said optical element is a spectacle lens.

5. The optical element of claim 3 wherein said light absorbing compound is a ultraviolet (UV) absorber and said photoinitiator is a UV initiator.

6. The optical element of claim 5 wherein said UV absorber has the general formula:

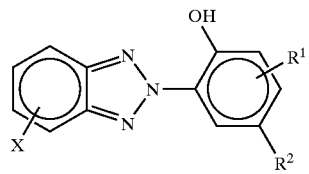

wherein X is selected from the group consisting of H and alkoxy radicals, preferably containing 1 to about 6 carbon atoms, $R^1$ is selected from the group consisting of H and alkyl radicals, preferably containing from 1 to 8 carbon atoms, provided that at least one of X and $R^1$ is other than H, $R^2$ is an organic radical with a terminal double bond, and said UV initiator has the general formula:

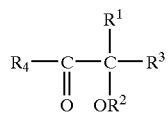
wherein $R^1$ is an organic radical having a terminal unsaturation; $R^2$ is alkyl, aryl, substituted alkyl or substituted aryl; $R^3$ and $R^4$ are independently selected from phenyls or substituted phenyls.
7. The optical element of claim 1 wherein said element is an intraocular lens.
8. The optical element of claim 1 wherein said optical element is a contact lens.
* * * * *

UNITED STATES PATENT AND TRADEMARK OFFICE
CERTIFICATE OF CORRECTION

PATENT NO.        : 6,851,804 B2
APPLICATION NO.   : 10/324540
DATED             : February 8, 2005
INVENTOR(S)       : Jagdish M. Jethmalani and Shiao H. Chang Page 1 of 1

It is certified that error appears in the above-identified patent and that said Letters Patent is hereby corrected as shown below:

Under (73) Assignee:
Insert --Calhoun Vision, Inc., Pasadena, CA (US)--.

Signed and Sealed this
Second Day of May, 2017

Michelle K. Lee
*Director of the United States Patent and Trademark Office*

UNITED STATES PATENT AND TRADEMARK OFFICE

(12)    CERTIFICATE EXTENDING PATENT TERM
        UNDER 35 U.S.C. § 156

| | | | |
|---|---|---|---|
| (68) | PATENT NO. | : | 6,851,804 |
| (45) | ISSUED | : | February 8, 2005 |
| (75) | INVENTOR | : | Jethmalani et al. |
| (73) | PATENT OWNER | : | RxSight, Inc. |
| (95) | PRODUCT | : | Light Adjustable Lens® (LAL) |

This is to certify that an application under 35 U.S.C. § 156 has been filed in the United States Patent and Trademark Office, requesting extension of the term of U.S. Patent No. 6,851,804 based upon the regulatory review of the product Light Adjustable Lens® (LAL) by the Food and Drug Administration. According to United States Patent and Trademark Office records, the original expiration date of the patent as of the date of issuance of this certificate is December 19, 2022. Because it appears that the requirements of the law have been met, this certificate extends the term of the patent for the period of

(94)                    5 years subject to the payment of maintenance fees as provided by law, with all rights pertaining thereto as provided by 35 U.S.C. § 156.

I have caused the seal of the United States Patent and Trademark Office to be affixed this 2nd day of January 2026.

John A. Squires
Under Secretary of Commerce for Intellectual Property and Director of the United States Patent and Trademark Office